United States Patent [19]

Zecchino et al.

[11] Patent Number: 5,008,100

[45] Date of Patent: Apr. 16, 1991

[54] OIL-IN-WATER EMULSIONS CONTAINING POLYETHYLENE

[75] Inventors: Julius R. Zecchino, Kinnelon, N.J.; Natrajan Krishnaswamy, Spring Valley, N.Y.; Pamela A. Clement, Clark; Anthony Vargas, Mahwah, both of N.J.

[73] Assignee: Elizabeth Arden Co., Division of Conopco, Inc., New York, N.Y.

[21] Appl. No.: 392,835

[22] Filed: Aug. 11, 1989

[51] Int. Cl.$^5$ ............................................... A61K 7/42
[52] U.S. Cl. ...................................... 424/59; 424/47; 424/60; 514/847; 514/947
[58] Field of Search .................. 514/847, 947; 424/60, 424/59, 47

[56] References Cited

U.S. PATENT DOCUMENTS

| | | | |
|---|---|---|---|
| 4,264,581 | 4/1981 | Kerkhof et al. | 424/59 |
| 4,797,272 | 1/1989 | Linn et al. | 424/59 |
| 4,797,273 | 1/1989 | Linn et al. | 424/59 |
| 4,869,897 | 9/1989 | Chatterjee et al. | 424/63 |

Primary Examiner—Jose G. Dees
Assistant Examiner—Deborah D. Carr
Attorney, Agent, or Firm—Milton L. Honig

[57] ABSTRACT

In accordance with this invention, a stable oil-in-water emulsion containing polyethylene which is an effective sunscreen composition is provided. The polyethylene is stable in the oil-in-water emulsion because of the presence of esters in the emulsion. The emulsions of the invention comprise: from about 0.5% by weight to about 30% by weight sunscreen agents; from about 0.2% by weight to about 5% by weight polyethylene; from about 0.5% by weight to about 20% by weight oil-in-water emulsion forming surfactants; from about 0.5% by weight to about 30% by weight esters; 0% to about 25% by about skin compatible non-silicone oils and hydrocarbons; 0% to about 30% by weight silicone oils; from about 0.1% to about 10% by weight humectants; and from about 20% to about 80% by weight water.

9 Claims, No Drawings

OIL-IN-WATER EMULSIONS CONTAINING POLYETHYLENE

BACKGROUND OF THE INVENTION

1. Field of the Invention

The present invention relates to a novel oil-in-water emulsion containing polyethylene and particularly to sunscreen compositions, in lotion and cream form, prepared therefrom.

2. Description of Related Art

Sunscreen compositions are commonly used during outdoor work or leisure for protection of exposed skin against painful sunburn. Many effective sunscreen preparations are sold commercially or are described in cosmetic or pharmaceutical literature. In general, sunscreen preparations are formulated in the form of a cream, lotion or oil containing as the active agent an ultraviolet radiation absorbing chemical compound. The active agent acts to block the passage of erythematogenic radiation thereby preventing its penetration into the skin.

The ideal sunscreen formulation should be non-toxic and non-irritating to skin tissue and be capable of convenient application to the skin in a uniform continuous film. The product should be sufficiently stable chemically and physically so as to provide an acceptable shelf life upon storage. It is particularly desirable that the preparation should retain its protective effect over a prolonged period after application. Thus, the active agent when present on the skin must be resistant to chemical or photodegradation, to absorption through the skin, and to removal by perspiration, skin oil, or water. For aesthetic reasons, the product should be substantially odorless (or be capable of being scented) and be non-staining to the skin or clothing.

Two agents known to be effective sunscreen agents are 2-ethylhexyl-N,N-dimethyl-p-aminobenzoate (also known as octyl dimethyl, p-aminobenzoic acid ester), and 2-hydroxy-4-methoxy benzophenone (also known as oxybenzone). In addition, other para amino benzoic acid derivatives, cinnamate derivates and salicylate derivatives known to those skilled in the art are available as sunscreen agents. Each of these compounds has been employed alone, or in combination, in various sunscreen preparations.

It is known that sunscreen compositions can be formulated from emulsions. For example, U.S. Pat. No. 4,797,272 describes various microemulsions for cosmetic uses which can include conventional sunscreen agents such as those mentioned above.

It has recently been discovered that the addition of polyethylene to a sunscreen composition greatly increases its innate sun protection factor. With this new technology, polyethylene can be used as a partial substitute for conventional sunscreen agents thereby lowering production costs of sunscreen compositions. Since conventional sunscreen agents can also cause some irritation to certain people, the use of polyethylene has the further advantage of mitigating such irritation. The polyethylene technology is the subject of a commonly owned co-pending application.

U.S. Pat. No. 4,264,581 discloses a water-in-oil emulsion sunscreen composition containing polyethylene. However, a water-in-oil emulsion carrier has certain disadvantages as compared to an oil-in-water emulsion carrier. For example, oil-in-water emulsions are generally perceived as having a better feel and texture than water-in-oil emulsions. Moreover, oil-in-water emulsions also provide a better undercoating for the subsequent application of additional cosmetics on top thereof. However, heretofore it has not been possible to formulate oil-in-water emulsions containing polyethylene since polyethylene is not stable in such emulsions.

Accordingly, it is an object of the invention to provide a stable oil-in-water emulsion which contains polyethylene.

It is a further object of the invention to provide a stable sunscreen composition in lotion and cream form formulated from an oil-in-water emulsion which contains polyethylene.

It is yet a further object of the invention to provide a sunscreen composition characterized by having a greater sun protection factor than sunscreen compositions containing the same level of sunscreen agents.

SUMMARY OF THE INVENTION

In accordance with this invention, a stable oil-in-water emulsion containing polyethylene which is an effective sunscreen composition is provided. The polyethylene is stable in the oil-in-water emulsion because of the presence of esters in the emulsion. The emulsions of the invention comprise: from about 0.5% by weight to about 30% by weight sunscreen agents; from about 0.2% by weight to about 5% by weight polyethylene; from about 0.5% by weight to about 20% by weight oil-in-water emulsion forming surfactants; from about 0.5% by weight to about 30% by weight esters; 0% to about 25% by weight skin compatible non-silicone oils and hydrocarbons; 0% to about 30% by weight silicone oils; from about 0.1% by weight to about 10% by weight humectants; and from about 20% by weight to about 80% by weight water. In cream form, the emulsions of the invention also include from about 0.5% by weight to about 10% by weight absorbents.

DETAILED DESCRIPTION OF THE INVENTION

An emulsion is a dispersed system containing at least two immiscible liquid phases, one of which is dispersed in the form of small droplets throughout the other, and an emulsifying agent (i.e., surfactant) in order to improve the stability of the system. Typically, one of the two immiscible liquids in an emulsion is aqueous while the other is an oil. Emulsions may be classified depending on which liquid forms the dispersion medium. An emulsion in which oil is dispersed as droplets throughout the aqueous phase is termed an oil-in-water emulsion. When water is the dispersed phase and an oil is the dispersion medium, a water-in-oil emulsion exists. Whether the aqueous phase or the oil phase becomes the dispersed phase, or is the dispersion medium, depends primarily on the emulsifying agent used and the relative amounts of the two liquid phases. Emulsified lotions and creams contemplated herein are the oil-in-water type wherein the continuous phase is water.

The instant invention provides a stable oil-in-water emulsion containing polyethylene in both lotion form and cream form. The emulsions comprise: from about 0.5% by weight to about 30% by weight sunscreen agents; from about 0.2% by weight to about 5% by weight polyethylene; from about 0.5% by weight to about 20% by weight oil-in-water emulsion forming surfactants; from about 0.5% by weight to about 30% by weight esters; 0% to about 25% by weight skin compatible non-silicone oils and hydrocarbons; 0% to about 30% by weight silicone oils; from about 0.1% by weight to about 10% by weight humectants; and from about 20% by weight to about 80% by weight water. If a cream form is desired, in addition to the foregoing components, the emulsions also include from about 0.5% by weight to about 10% by weight absorbents. The emulsions can also include effective amounts of thickeners/viscosifiers and preservatives.

In general, the individual components used in the formulation should be of a quality or purity (such as U.S.P. or N.F.) suitable for cosmetic use.

An example of a preferred polyethylene which can be employed in the compositions is a homopolymer having an average molecular weight of about 1500. A polyethylene homopolymer acceptable for use in the compositions of the present invention is available from Allied Chemical Company, Morristown, N.J. under the name "A-C® Polyetheylene 617." This polyethylene exhibits the following characteristics:
Softening point (ASTM E-28): 102° C.
Hardness (ASTM D-5): 8 dmm
Visocisity (Brookfield), 140° C.: 180
Density (ASTM D-1505): 0.91 g/cc
Many other grades of polyethylene having a wide range of physical characteristics may also be employed.

When it is included in the composition, the polyethylene is a film former and acts like an active sunscreen ingredient. The sun protection factor (SPF) of the sunscreen formulation increases unexpectedly and dramatically with the addition of polyethylene. The composition of the present invention includes levels of polyethylene ranging from about 0.2% to about 5% by weight. The composition achieves a greater sun protection factor than other compositions which have the same levels of conventional sunscreen agents (i.e., oxybenzone and octyldimethyl p-aminobenzoic acid).

The sunscreen agents employed in the oil-in-water emulsions can be conventional sunscreen agents including PABA derivatives, cinnamate derivates and salicylate derivates. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trade names Parsol MCX and Benzophenone-3, respectively. The exact amount of sunscreen employed in the emulsions can vary depending upon the degree of protection desired from the sun's UV radiation. Preferably, the emulsion contains a total of about 5%-12% by weight of sunscreen agents, and most preferably about 7%-9% by weight.

The surfactants used in the emulsions must be those which form an oil-in-water emulsion. These surfactants are well known to formulation chemists skilled in the art. The surfactants can comprise from about 0.5% by weight to about 20% by weight of the emulsions, preferably from about 2% by weight to about 12% by weight. Surfactants may be cationic, nonionic or anionic in nature. Preferably, nonionic surfactants are employed in the present emulsions because they are non-irritating to skin. Anionic and cationic surfactants may also be employed, but care should be taken to make the resulting compositions as nonirritating as possible.

Suitable nonionic surfactants include polymeric ethers, alkoxylated amines and the combination of alkoxylated alcohols together with sorbitan derivatives (for example, the combination of ceteth 10 and sorbitan stearate). A suitable cationic surfactant is diethanolamine cetyl phosphate. A suitable anionic surfactant is sodium lauryl sulfate.

Preferred surfactants are the reaction products of triethanolamine (TEA) or potassium or sodium with stearic acid or myristic acid or palmitic acid. Specific preferred surfactants for use in forming the emulsions are GMS/PEG-100 Stearate (a blend of glyceryl stearate and polyethylene glycol-100 stearate), isostearic acid, cetearyl alcohol, choleth-24, ceteath-24 and the reaction product of stearic acid and triethanolamine. When the surfactant is a reaction product, it may be formed in situ when the emulsion is prepared.

The emulsions of the invention may also contain one or more cosurfactants in addition to the surfactants described above. Exemplary cosurfactants suitable for use herein include fatty aliphatic alcohols having from 12 to 18 carbon atoms, such as cetyl alcohol or myristyl alcohol.

A variety of skin compatible non-silicone oils and long chain hydrocarbons may also be employed in the emulsions of the invention which are known and commonly used by those of ordinary skill in the art. Collectively, the non-silicone oils and hydrocarbons can comprise up to about 25% by weight of the emulsion, preferably from about 1% by weight to about 7% by weight Exemplary hydrocarbons include hydrocarbon straight chain alkyl compounds having from 12 to 18 carbon atoms, and hydrocarbon branched alkyl compounds having from 12 to 30 carbon atoms. Specific examples of acceptable long chain hydrocarbons include squalane, mineral oil and squalene.

Acceptable animal oils for use in the emulsions include cod liver oil, lanolin oil, mink oil, orange roughy oil and shark liver oil. Acceptable vegetable oils include almond oil, apricot kernel oil, avocado oil, castor oil, coconut oil, corn oil, evening primrose oil, jojoba oil, olive oil, safflower oil, sesame oil, soybean oil, and wheat germ oil.

The silicone oils which can be used in the emulsions of the invention can be selected from a variety of polysiloxane compounds and can comprise up to about 30% by weight of the composition, preferably from about 1% by weight to about 6% by weight. These polysiloxanes may be volatile or non-volatile and include the cyclic dimethyl polysiloxanes having from three to six silicon atoms, such as cyclomethicone, as well as linear polysiloxanes having a viscosity of ten centistokes, or less, at room temperature (25° C.), and mixtures thereof. A preferred polysiloxane employed in the compositions of the invention is cyclomethicone.

The emulsions of the invention can also contain one or more suitable skin compatible humectants in amounts ranging from about 0.1% by weight to about 10% by weight of the composition, preferably from about 2% by weight to about 9% by weight. These humectants are polar in nature and include, for example, propylene glycol, glycerine, sorbitol and other polyhydric alcohols.

All cosmetic compositions must be protected against the growth of potentially harmful microorganisms, and therefore preservatives are added as a routine. While it is in the aqueous phase that microorganisms tend to grow, microorganisms can also reside in the oil phase. As such, preservatives which have solubility in both water and oil are preferably employed in the present compositions. The traditional preservatives for cosmetics and pharmaceuticals are alkyl esters of parahydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives for a preferred emulsion product of this invention are methyl paraben, imidazolidinyl urea, sodium dehydroxyacetate, propyl paraben and benzyl alcohol. The preservatives should be selected having regard for the use of the composition and possible incompatibilities between the preservatives and other ingredients in the emulsion. The preservatives are preferably employed in amounts ranging from 0.5% by weight to 2% by weight of the composition.

The emulsions of the invention can also include effective amounts of thickeners/viscosifiers in amounts up to about 5% by weight of the composition. As known to those skilled in the art, the precise amount of thickeners can vary depending upon the consistency and thickness of the composition which is desired. Exemplary thickeners are xanthan gum and carbopol-941. A preferred thickener/viscosifier is glyceryl stearate which also functions as an emulsifier.

In cream form, the emulsions preferably include from about 0.5% by weight to about 10% by weight of absorbents. Preferred absorbents are Nylon 12 and aluminum starch octenyl succinate. The latter is commercially available under the trade name Dri Flo.

The addition of esters to the oil-in-water emulsions is necessary in order to render the polyethylene stable in the emulsions. The esters can comprise from about 0.5% by weight to about 30% by weight of the emulsion, preferably from about 3% by weight to about 15% by weight. Suitable esters are fatty acid esters and diesters.

Acceptable examples of fatty diesters include dibutyl adipate, dibutyl sebacate, dicetyl adipate, diethyl sebacate, dihexyl adipate, diisocetyl adipate, diisopropyl adipate, diisopropyl dimerate, diisopropyl sebacate, diisostearyl adipate, dioctyl adipate, dioctyl sebacate, and dioctyl succinate.

Acceptable branched chain fatty esters include 2-ethylhexyl isonomanoate, 2-ethylhexyl myristate, 2-ethylhexyl oxystearte, 2-ethylhexyl palmitate, 2-ethylhexyl pelargonate, 2-ethylhexyl stearate, isocetyl isodecanoate, isocetyl palmitate, isodecyl isononanoate, isononyl isononanoate, isopropyl isostearate, isopropyl laurate, isopropyl linoleate, isopropyl myristate, isopropyl oleate, isopropyl palmitate, isopropyl stearate, isostearyl isostearate, isostearyl lactate, isostearyl neopentanoate, isostearyl palmitate, ispridecyl isononanoate, and tocopheryl linoleate.

Acceptable tribasic acid esters include triisocetyl citrate, triisopropyl trilinoleate, triisostearyl trilinoleate, trilauryl citrate, and trioctyl citrate.

Acceptable straight chain fatty esters include lauryl lactate, lauryl myristate, lauryl palmitate, lauryl stearate, myristyl lactate, myristyl myristate, myristyl neopentanoate, myristyl propionate, myristyl stearate, oleyl erucate, oleyl linoleate, oleyl myristate, oleyl oleate, oleyl stearate, stearyl lactate and stearyl oleate.

Preferred esters include coco-caprylate/caprate (a blend of coco-caprylate and coco-caprate), propylene glycol myristyl ether acetate, diisopropyl adipate and cetyl octanoate. Propylene glycol myristyl ether acetate is commercially available under the trade name Hetester PMA and is most preferred because its presence also enhances the sun protection factor of the sunscreen compositions.

In preparing the emulsions, typically, an oil phase is prepared by combining all hydrophobic components, as well as the water-insoluble solids, in a container and heating the resulting mixture under agiation until all the ingredients are dissolved. The polyethylene is added to the oil phase at elevated temperatures of the oil phase in the range of 90°–95° C. High speed agitation/mixing is conducted to ensure the intimate blending of the polyethylene. In a separate container, an aqueous phase is prepared by combining all of the hydrophilic components, as well as the oil-insoluble solids, and heating the resulting mixture under constant stirring until the mixture is homogeneous. The phases thus prepared are combined and stirred until homogeneous. The composition is finally allowed to stand for approximately 24 hours in order for the emulsion to achieve equilibrium. The composition may be transferred to appropriate containers for storage until needed for application.

The invention will now be described in greater detail with reference to the following examples. The examples are not intended to be limiting as to the scope of the present invention in any respect and should not be so construed.

EXAMPLE 1

A sunscreen lotion was prepared as follows:

| PHASE | ITEM | WGT % |
|---|---|---|
| A | Carbopol-941 | 0.10 |
|   | Deionized Water | 65.60 |
| B | Glycerin | 4.50 |
|   | Xanthan Gum | 0.10 |
|   | Disodium EDTA | 0.20 |
| C | Allantoin | 0.20 |
|   | dl-Panthenol | 1.00 |
|   | Triethanolamine | 0.30 |
| D | Polyethylene 617 | 1.00 |
| E | Methylparaben | 0.30 |
|   | Stearic Acid TP | 0.50 |
|   | GMS/PEG-100 Stearate (a blend of glyceryl stearate and polyethylene glycol-100 stearate) | 2.00 |
|   | Cetyl Alcohol | 1.00 |
|   | Isostearic Acid | 2.50 |
|   | Robane (Squalane) | 2.80 |
|   | Amerchol L-101 (A mixture of mineral oil and lanolin alcohol) | 1.00 |
|   | Tenox IV (A mixture of corn oil and BHA and BHT) | 0.05 |
|   | Propylparaben | 0.15 |
|   | Parsol MCX | 5.00 |
|   | Benzophenone-3 | 2.00 |
|   | Cyclomethicone 344 | 2.00 |
|   | Coco-Caprylate/Caprate (a blend of coco-caprylate and coco-caprate) | 2.00 |
|   | Vitamin A Palmitate (Retinyl Palmitate) | 0.10 |
|   | Vitamin E Linoleate (Tocopheryl Linoleate) | 0.50 |
|   | Hetester PMA | 3.00 |
|   | Cerasynt SD (Glyceryl Stearate) | 0.25 |
|   | Cetearyl Alcohol | 0.25 |
|   | Solulan C-24 (Choleth-24 and Ceteath-24) | 0.25 |
| F | Benzyl Alcohol | 0.50 |
|   | Sodium Dehydroxyacetate ("DHA") | 0.10 |
|   | Germall 115 (Imidazolidinyl Urea) | 0.50 |
| G | Fragrance | 0.25 |

Phase A was prepared by sprinkling carbopol-941 into the water under constant stirring in a sanitized vessel equipped with a propeller stirrer. The mixture was stirred until the carbopol-941 was well dispersed and hydrolyzed. Fish-eyes were avoided during the process.

In preparing Phase B, the xanthan gum was sprinkled on the glycerin in a sanitized vessel, under constant stirring to ensure proper dispersal. The disodium EDTA was subsequently added under constant stirring.

Phase B was added to Phase A under constant stirring. Stirring was continued until the xanthan gum was completely hydrolyzed. Phase C was added to Phase AB under constant stirring until Phase ABC was uniform. Stirring was continued as the Phase ABC was heated to a temperature of 90°-95° C.

The ingredients of Phase E were weighed into a sanitized vessel equipped with a propeller stirrer. Phase E was heated to 90°-95° C. under constant stirring. When Phase E was uniform at this temperature, Phase D was slowly sprinkled in under constant stirring. Stirring was continued until the Phase DE was uniform and clear. The temperature was maintained in the range of 90°-95° C. at all times. Phase DE was then added to Phase ABC under constant stirring, while the temperature was maintained in the range of 90°-95 C.

When Phase ABCDE was uniform, homogenizing was started under rapid cooling at a rate of 2° C./minute. The inner wall of the container was scraped continuously. When the temperature of Phase ABCDE fell to 45°-50° C., the ingredients of Phase F were added separately as homogenization was continued.

When the temperature fell to 40°-45° C., Phase G was added to Phase ABCDEF and homogenization was continued until the temperature dropped to 20° C. The batch was held at this temperature for 24 hours. The resulting lotion proved to be an effective sunscreen composition wherein the polyethylene remained stable therein.

EXAMPLE 2

A sunscreen cream was prepared as follows:

| PHASE | ITEM | WGT % |
| --- | --- | --- |
| A | Deionized Water | 20.00 |
|   | Carbopol 941 (carbomer 941) | 0.10 |
| B | Butylene Glycol | 3.00 |
|   | Dri Flo (Aluminum starch Octenyl Succinate, an absorbent) | 2.00 |
| C | Deionized Water | 33.75 |
|   | Xanthan Gum | 0.20 |
|   | Butylene Glycol | 1.00 |
|   | Allantoin | 0.20 |
|   | Dl Panthenol | 1.00 |
|   | Disodium EDTA (preservative) | 0.20 |
| D | GMS/PEG100 Stearate | 2.00 |
|   | Stearic Acid | 3.00 |
|   | Cetyl Alcohol | 3.00 |
|   | GMS, Non-Emulsifying (Glyceryl Stearate) | 0.50 |
|   | Cetearyl Alcohol | 0.50 |
|   | Jojoba Oil | 2.00 |
|   | Tenox IV | 0.05 |
|   | Hetester PMA | 3.00 |
|   | Diisopropyl Adipate | 2.00 |
|   | Cetyl Octanoate | 2.00 |
|   | Octyl Methoxycinnamate | 7.00 |
|   | 2 Hydroxy 4 Methoxybenzophenone | 2.00 |
|   | Silicone Fluid 200, 100 cts | 0.20 |
|   | Methylparaben | 0.30 |
|   | Ethylparaben | 0.15 |
|   | Nylon 12 (an absorbent) | 1.00 |
|   | Polyethylene 617 | 1.00 |
| E | Deionized Water | 2.00 |
|   | Triethanolamine 98% | 0.30 |
| F | SiliCone Fluid 344 (Cyclomethicone) | 2.50 |
| G | Sodium DHA | 0.10 |
| H | Deionized Water | 2.00 |
|   | Germall 115 | 0.50 |
| I | Vitamin E Linoleate | 0.50 |
|   | Vitamin A Palmitate | 0.10 |
|   | Benzyl Alcohol | 0.60 |
| J | Fragrance | 0.25 |

Phase A was prepared by sprinkling into each of two sanitized drums half the amount of carbopol 941 with half the amount of cold water and mixing with vigorous agitation until completely hydrated. Care was taken to avoid the formation of fish eyes.

In a sanitized vessel, Phase B was pre-mixed by sprinkling the Dri Flo into the butylene glycol with vigorous agitation. Phase B was mixed until smooth and uniform and was held for later addition.

Xanthan gum was mixed with the butylene glycol of Phase C until smooth and uniform. Deionized water was next added to the main vessel and mixed until smooth and uniform with vigorous agitation. The remaining Phase C ingredients were added in and mixed until dissolved. The mixture was heated to and maintained at a temperature of 90°-95° C.

Phase D was weighed out into a suitable container equipped with a propeller stirrer, holding out the nylon, polyethylene, methylparaben, ethylparaben, 2 hydroxy-4-methoxy benzophenone, and the octyl methoxycinnamate. The mixture was heated to 90°-95° C. and mixed until homogeneous. The methylparaben and ethylparaben were mixed in until the mixture was clear. The sunscreen agents were then added in and mixed until clear. Next, the nylon was sprinkled in until dispersed. The polyethylene was then mixed in until the solution was free of granules.

Phase D was added to Phase C with homomixing and sidesweep and mixed until homogeneous. Phase E was added to Phase CD. Phase B was then added to Phase CDE. During these addition steps, homomixing and sidesweep were continuously effected to prevent agglomeration of Dri Flo on sidewalls. Once the mixture was homogeneous, cooling was immediately begun. Continuous mixing took place while cooling to 45°-50° C.

Phase F was added at 45°-50° C. and mixed in until homogenous. Phase G and then Phase H were next mixed in until homogenous. Phase I was added at 40° C. and mixed until homogenous. Cooling continued to 32°-36° C.

Phase A was then added and the mixture was allowed to pass through the homogenizer only until uniform. Homomixing was stopped at this point. Mixing continued from this point only with the sweepblade. Phase J was then added and the product was mixed and cooled to 25° C.

The product was discharged immediately into sanitized drums. The product proved to be an effective sunscreen cream wherein the polyethylene remains stable therein.

What is claimed is:

1. A stable oil-in-water emulsion sunscreen composition comprising from about 20% by weight to about 80% by weight water, from about 0.5% by weight to about 20% by weight oil-in-water emulsion forming surfactants, from about 0.5% by weight to about 30% by weight propylene glycol myristyl ether acetate, from about 0.2% by weight to about 5% by weight polyethylene, from about 0.5% by weight to about 30% by weight sunscreen agents, from about 0.5% by weight to about 10% by weight absorbents selected from the group consisting of aluminum starch octenyl succinate and nylon, from about 0.1% by weight to about 10% by weight humectants, 0% to about 25% by weight skin compatible non-silicone oils and hydrocarbons, and 0% to about 30% by weight silicone oils.

2. The composition according to claim 1 wherein the surfactants are selected from the group consisting of glyceryl stearate, polyethylene glycol-100 stearate, cetearyl alcohol, isosteaeric acid and the reaction product of stearic acid and triethanolamine.

3. The composition according to claim 1 further comprising up to about 5% by weight of thickeners.

4. The composition according to claim 1, in lotion form, consisting essentially of the following ingredients:

| Classification | Ingredient | Weight Percent |
|---|---|---|
| esters | propylene glycol myristyl ether acetate | 3.0 |
| | coco-caprylate/caprate | 2.0 |
| humectants | glycerin | 4.5 |
| silicone oils | cyclomethicone | 2.0 |
| hydrocarbons and non-silicone oils | squalane | 2.8 |
| | mineral oil and lanolin | 1.0 |
| surfactants | GMS/PEG - 100 stearate (a blend of glyceryl stearate and polyethylene glycol-100 stearate) | 2.0 |
| | triethanolamine | 0.3 |
| | stearic acid | 0.5 |
| | cetyl alcohol | 1.0 |
| | isostearic acid | 2.5 |
| thickeners | carbomer-941 | 0.1 |
| | xanthan gum | 0.1 |
| sunscreen agents | octyl methoxycinnamate | 5.0 |
| | 2 hydroxy 4 methoxybenzophenone | 2.0 |
| polyethylene | polyethylene 617 | 1.0 |
| preservatives | imidazolidinyl urea | 0.5 |
| | benzyl alcohol | 0.5 |
| | propylparaben | 0.15 |
| | methylparaben | 0.3 |
| water | water | remainder |

5. A stable oil-in-water emulsion sunscreen composition comprising from about 45% by weight to about 80% by weight water, from about 3% by weight to about 15% by weight propylene glycol myristyl ether acetate, from about 2% by weight to about 12% by weight oil-in-water emulsion forming surfactants, from about 0.2% by weight to about 5% by weight polyethylene, from about 5% by weight to about 12% by weight sunscreen agents, from about 2% by weight to about 9% by weight humectants, from about 1% by weight to about 6% by weight silicone oils, from about 1% by weight to about 7% by weight skin compatible non-silicone oils and hydrocarbons, from about 0.1% by weight to about 3% by weight thickeners, and from about 1% by weight to about 7% by weight absorbents selected from the group consisting of aluminum starch octenyl succinate and nylon.

6. The composition according to claim 5 further comprising from about 0.5% by weight to about 2% by weight preservatives.

7. The composition according to claim 5 wherein the skin compatible non-silicone oils and hydrocarbons are selected from the group consisting of squalane, mineral oil, lanolin and mixtures thereof.

8. The composition according to claim 5 in cream form consisting essentially of the following ingredients:

| Classification | Ingredient | Weight Percent |
|---|---|---|
| esters | diisopropyl adipate | 2.0 |
| | cetyl octanoate | 2.0 |
| | propylene glycol myristyl ether acetate | 3.0 |
| humectants | butylene glycol | 4.0 |
| silicone oils | cyclomethicone | 2.5 |
| | dimethicone | 0.2 |
| hydrocarbons and non-silicone oils | jojoba oil | 2.0 |
| surfactants | GMS/PEG 100 stearate | 2.0 |
| | stearic acid | 3.0 |
| | cetearyl alcohol | 0.5 |
| | cetyl alcohol | 3.0 |
| | triethanolamine | 0.3 |
| thickeners | carbomer 941 | 0.1 |
| | xanthan gum | 0.2 |
| sunscreen agents | octyl methoxycinnamate | 7.0 |
| | 2 hydroxy 4 methoxybenzophenone | 2.0 |
| polyethylene | polyethylene 617 | 1.0 |
| preservatives | methylparaben | 0.3 |
| | ethyl paraben | 0.15 |
| | imidazolidinyl urea | 0.5 |
| | benzyl alcohol | 0.6 |
| water | water | remainder. |

9. The composition according to claim 5 wherein the polyethylene has an average molecular weight of about 1500.

* * * * *